United States Patent [19]

Feaster

[11] 4,327,746

[45] May 4, 1982

[54] BLOOD EXTRACTION DEVICE

[75] Inventor: William W. Feaster, Monte Carlo, Monaco

[73] Assignee: C. A. Greiner & Sohne GmbH & Co. KG, Nurtigen, Fed. Rep. of Germany

[21] Appl. No.: 127,709

[22] Filed: Mar. 6, 1980

[30] Foreign Application Priority Data

Mar. 7, 1979 [DE] Fed. Rep. of Germany ....... 2908817
Nov. 19, 1979 [DE] Fed. Rep. of Germany ....... 2946660

[51] Int. Cl.³ .............................................. A61B 5/14
[52] U.S. Cl. .................................................. 128/764
[58] Field of Search ....................... 128/764, 766, 272

[56] References Cited

U.S. PATENT DOCUMENTS

| | | | |
|---|---|---|---|
| 3,326,206 | 6/1967 | Barr, Sr. et al. | 128/764 |
| 3,536,061 | 10/1970 | Ogle | 128/764 |
| 4,155,350 | 5/1979 | Percarpio | 128/764 |
| 4,166,450 | 9/1979 | Abramson | 128/764 |
| 4,216,782 | 8/1980 | Sarstedt | 128/764 |

FOREIGN PATENT DOCUMENTS

935123 1/1948 France ................................ 128/764
1278387 10/1961 France ................................ 128/764

*Primary Examiner*—John D. Yasko
*Attorney, Agent, or Firm*—Michael F. Petock

[57] ABSTRACT

A blood extraction device includes a hollow, cylindrical receptacle which is open at one end with a double-ended hollow needle at its other end, into which an evacuated blood sample tube is inserted. The blood sample tube is closed by means of a screw-attachment cap, whereby the cap retains a sealing membrane against the blood sample tube in order to close it tightly. A device for evacuation of blood sample tubes is provided. A second needle may be provided at the closed end of the receptacle, via which needle the inserted blood sample tube may be connected with a suction line, which is formed, in one embodiment, by a compressible elastic balloon and a valve.

6 Claims, 10 Drawing Figures

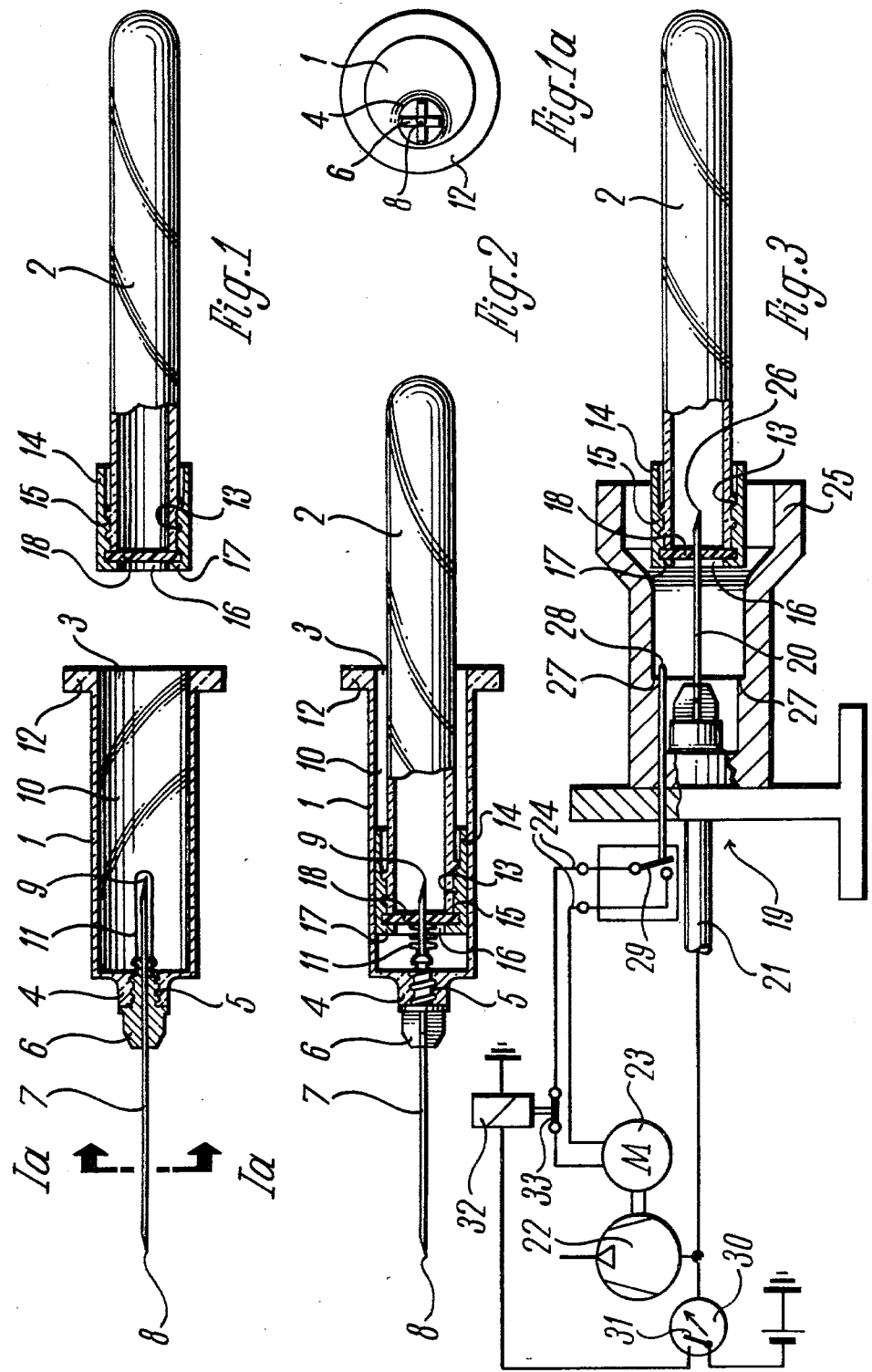

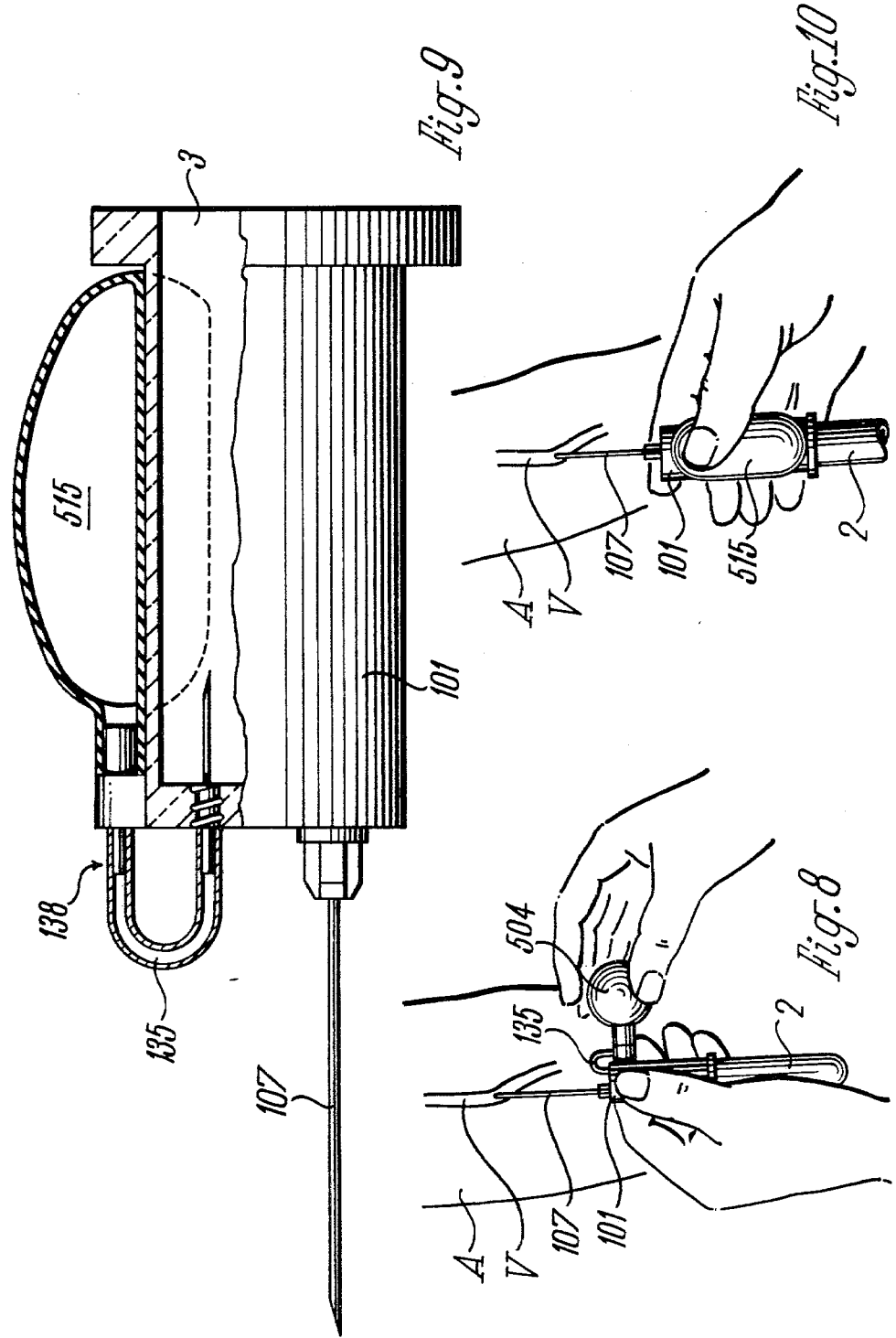

BLOOD EXTRACTION DEVICE

BACKGROUND OF THE INVENTION

The present invention is directed to a blood extraction device as described hereinafter, and in addition, a procedure for using it, and a device for execution of a procedural step in the use of the blood extraction device.

Blood extraction devices are generally known, for example see U.S. Pat. Nos. 2,460,641 and 3,136,440. In the prior art, the seal of the blood sample tube consists of a rubber stopper. If this stopper is opened in order to remove the extracted blood for further use or analysis, a certain momentary low pressure will occur at the surface of the blood sample, with the result that some drops of the blood sample may be scattered when the stopper is removed. This "aerosol" effect is reinforced by the elasticity of the stopper material when it is opened rapidly. The danger of this "aerosol" effect may be particularly grave if the inside surface of the stopper is covered by test liquid due to sequential handling of the blood sample tube; in such a case, individual droplets are figuratively thrown off the surface when the stopper is rapidly opened. This effect may have inherent infection risks. The staff member comes into contact with a patient's blood, which may be infected. It is also a major consideration that in this manner, cross-contamination of samples may occur in the laboratory. For this reason, stopper removers have been specifically developed as separate devices. However, to utilize a specific tool for opening the sample tubes is impractical, even if the clinic staff does become accustomed to this procedure.

Since, in the case of the known devices, the vacuum is created already in the production stage, the seal must be designed so that it maintains the vacuum for a longer period of time. The rubber stopper must be thick at the edge. Frequently, penetration by a hollow needle requires too much force. For this reason, a recess is provided in the center of the stopper, in order to have a thinner place for penetration. Thus, the needle cannot be inserted close to the side, i.e. eccentrically, which would be desirable in order to make a "flatter" insertion into the patient's vein. Furthermore, in the case of known tubes, there may be the disadvantages that according to the age of the tube, the initially uniform vacuum may have decreased so that there is no guarantee of constant and uniform speed of blood extraction, nor for a constantly uniform volume of the extracted sample.

SUMMARY OF THE INVENTION

The present invention provides a new, unobvious and advantageous blood extraction device. The present invention eliminates the dangers of an "aerosol" effect during the opening of the blood sample tube. In addition, sealing of the blood sample tube is simplified and more reliable results are achieved as the vacuum in the blood sample tube is more uniform at the time of use.

The invention solves the above-mentioned problem in a particularly simple manner by using a relatively thin and simple sealing material, the membrane, in combination with a screw closure. This allows, for the first time, the application of a screw closure in a blood extraction system under vacuum of the above-mentioned nature, although the rubber stopper has been regarded as indispensable for the sake of penetration with a needle. This prejudice has now been removed by means of the invention. The membrane can be manufactured of relatively thin and/or softer material, so that it is easier to penetrate and requires only approximately ⅓ of the force. The needle can also be placed eccentrically. The disadvantage which was originally feared, namely that the sealing be insufficient, is overcome by means of another extreme simplification of the use, namely that the tubes must not be evacuated at the outset, but the evacuation is performed shortly before use. That is, the number of tubes to be used in one day are evacuated at the beginning of that day. This is accomplished by means of a simple pump which can be connected with the interior of the tube, also via a needle by means of which the membrane can be penetrated. This also has the advantage that a blood sample tube where the vacuum was erroneously eliminated, that is by means of a mistaken penetration, may be evacuated again.

Thus, a simple, constructive design is accomplished. Particularly, the design is simple when compared to blood extraction systems which, in principle, function as syringes in order to obtain a vacuum.

A further advantage of the present invention concerns blood extraction under aspiration, that is under control of a negative pressure in the blood sample tube in a particularly simple manner. In one embodiment, a rubber balloon is provided for this purpose. Thereby, it is particularly simple to control the negative pressure in the blood sample tube and consequently the rate at which blood is extracted from a patient, by means of compression and controlled release of the rubber balloon. The rubber balloon may also be used as a handle. A valve is provided between the rubber balloon and a second needle, which serves aspiration purposes. The valve prevents air pressure from entering the blood sample tube when the rubber balloon is compressed, and also activates the suction or negative pressure in the blood sample tube when the rubber balloon is released. The rubber balloon may also be constructed in the shape of a fish bladder and located alongside and adjacent to the outside of the receptacle. In this manner, it is particularly simple to handle the device with a single hand.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

FIG. 1 is a side elevation view partially in cross-section, of a blood extraction device in accordance with the present invention.

FIG. 1a is a view, partially in cross-section, taken along line 1a—1a of FIG. 1.

FIG. 2 is an elevation view, partially in cross-section, of an embodiment of the present invention illustrating the elements of FIG. 1 in partially assembled form.

FIG. 3 is a view, partially in cross-section and partially in schematic form, illustrating a blood sample tube in accordance with the present invention being connected to an evacuation device in accordance with the present invention.

FIG. 8 is an elevation view illustrating a manner of use of the apparatus of FIG. 7 in extracting blood from a vein.

FIG. 9 is an elevation view, partially in cross-section, of another embodiment of the present invention.

FIG. 10 is an elevation view illustrating a manner of use of the apparatus of FIG. 9 in extracting blood from a vein.

DETAILED DESCRIPTION OF PREFERRED EMBODIMENTS

Figure 4A:
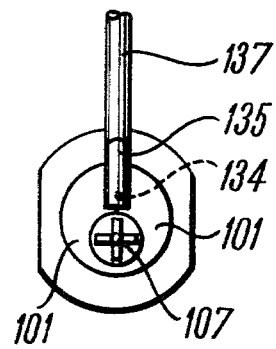
FIGS. 4a, 4b and 4c illustrate another embodiment of the present invention, with FIG. 4a being a front elevation view looking down needle 107, FIG. 4b being a side elevation view partially in cross-section and FIG. 4c being a top elevation view of FIG. 4b.

The blood extraction device according to FIGS. 1 through 3 is comprised of a receptacle 1 and a blood sample tube 2. Receptacle 1 has a hollow cylindrical shape and is open at its one end 3. At its other end 4, receptacle 1 is provided with threading 5, into which needle holder 6 is screwed, eccentrically as shown in FIG. 1a. Needle holder 6 serves as a firm attachment for double-ended hollow needle 7, one end 8 of which is located, as shown, outside of receptacle 1 and is inserted into the vein of a person for purposes of blood extraction, and the other end 9 of which extends into the interior of hollow cylindrical space 10 of receptacle 1. That part of needle 7 which extends into the interior 10 of the receptacle is surrounded by protective cover 11 of easily penetrated, light, soft material. At end 3, receptacle 1 is provided with flange 12 which facilitates the handling during blood extraction.

Preferably, blood sample tube 2 is manufactured of transparent synthetic material, e.g. polystyrol or polypropylene. Blood sample tube 2 is provided with a screw closure, comprised of cap 14 screwed on to the left end, as seen in FIG. 1, of blood sample tube 2. Blood sample tube 2 is provided with screw threads which mate with corresponding threading 15 of cap 14. Further, cap 14 is provided with an opening 16, the diameter of which is designed so that edge or rim 17, which extends from the outside inwardly and perpendicularly to the axis of blood sample tube 2, extends so far that it presses membrane 18 against the open front of blood sample tube 2 at its open end, left end seen in FIG. 1. Thereby, the interior of blood sample tube 2 is sealed, so that a vacuum can be maintained in the tube. Membrane 18 is comprised of soft rubber, which has the characteristic that when a needle penetrates it and is removed again, the material closes again. Such materials are known in the art. The thickness of membrane 18 amounts to 1.5 to 3 mm, preferably 2 mm.

The exterior of cap 14 is cylindrically designed so that it fits into hollow cylindrical space 10 of receptacle 1. Thus, blood sample tube 2 with attached cap 14 can be inserted into receptacle 1 as shown in FIG. 2. Thereby, end 9 of needle 7 penetrates membrane 18. By the inner penetration of hollow needle 7, a connection is created between the interior of blood sample tube 2 and the opening of needle 7 at its end 8. Shortly before tip 9 of needle 7 penetrates into membrane 18, protective cover 11 on tip 9 of needle 7 is penetrated. When pushed further in, as shown in FIG. 2, protective cover 11 compresses like a bellows.

Initially, blood sample tubes are prepared in the manner shown in FIG. 2, where they are closed and vacuum sealed. They are initially not evacuated. Thus, the blood extraction device according to the present invention differs from all known blood extraction systems working with a vacuum, insofar as blood sample tube 2 is first made available in a status of not being evacuated, i.e., it is marketed and delivered to the user not evacuated.

Not until shortly before use, that is probably at the beginning of the day, in quantities required for one day's use, or immediately prior to use of the blood extraction device, is vacuum created in blood sample tubes 2 which have previously been tightly closed. This is accomplished in the manner shown in FIG. 31. The tightly closed, but not yet evacuated, blood sample tube 2 is evacuated in a simple evacuation device. This evacuation device 19 is comprised of a hollow needle 20, which is connected to a vacuum pump 22 via a line 21. The vacuum pump 22 is activated by means of electrical motor 23, supplied with current via lines 24. Further, evacuation device 19 is provided with insertion funnel 25 surrounding the needle. Blood sample tube 2 can be inserted into the funnel so that end 26 of needle 20 penetrates membrane 18. If blood sample tube 2 is inserted so far that edge 17 touches collar 27 which forms a buffer, it simultaneously moves feeler 28 so far that it closes working contact 29 which is mechanically coupled to it. This working switch is located in electrical line 24, which is switched so, in relation to electrical motor 23, that motor 23 is activated when working contact 29 is activated. Thus, vacuum pump 22 is activated when blood sample tube 2 is inserted into insertion funnel 25, and blood sample tube 2 is evacuated. Simultaneously, via pressure meter 30 connected via line 21, the vacuum is measured in line 21 and, consequently, in blood sample tube 2 as well. When a specific predetermined nominal value has been reached, working contact 31 in pressure meter 30 will close, which working contact 31 interrupts line 24 via relay 32 and its rear contact 33, thus deactivating electrical motor 23 and, consequently, vacuum pump 22. Thereafter, blood sample tube 2 is removed from needle 20, and is then ready for use.

Blood extraction from a patient proceeds in the following manner. First, one takes receptacle 1, where blood sample tube 2 is only inserted so far that membrane 18 is not yet penetrated, and point 8 is inserted into the vein of a patient. Then blood sample tube 2 is inserted further into interior space 10, until point 9 penetrates membrane 18. The vacuum in blood sample tube 2 extracts blood from the vein. When a sufficient quantity of blood has been extracted, blood sample tube 2 is removed from receptacle 1. Membrane 18 closes again, and the blood extraction procedure is complete. The blood sample can then be removed from blood sample tube 2 when cap 14 is removed.

Figure 4B:
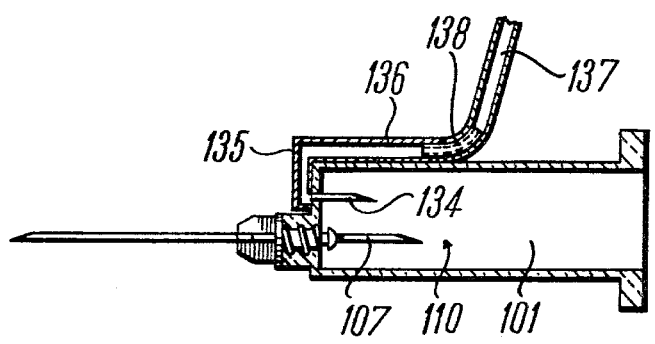
Figure 4C:
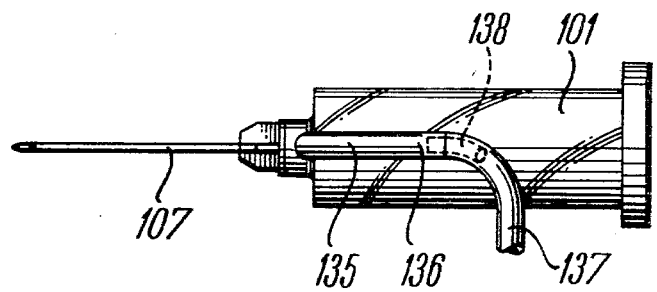

FIGS. 4a through 4c show another embodiment. Receptacle 101 is provided with two needles, namely first needle 107 and second needle 134. Needle 134 transforms into hollow line 135, which first runs radially to the outside of receptacle 101 and then along the cylindrically outside wall. At end 136 of hollow line 135, there is a suction line 137 connected with a plug connector, for purposes of aspiration during the blood extraction process. This means, if, as shown in FIG. 2, a blood sample tube is inserted so far into cylindrical interior space 110 of receptacle 101 that the two needles 107 and 134 penetrate membrane 18 of blood sample tube 2, the blood extraction can be aided. If one sucks at the suction line, the vacuum in blood sample tube 2 is increased. If air is let in, blood extraction is terminated. In this manner it is possible to control the blood extraction process as desired.

The blood extraction system of the present invention is simplified over that of the prior art since the vacuum in blood extraction tube 2 only need be maintained for a short period of time, approximately the duration of one day and often less, since the vacuum in blood extraction tube 2 is created only relatively shortly before the use of the blood extraction system, as described in relation to FIG. 3. The result is that one can be certain of the existence of a vacuum in blood extraction tube 2 at the time the blood extraction system of the present invention is being used. Furthermore, this vacuum also has a very specific value. Thus, a particular rate of speed of blood extraction is guaranteed. With the aid of the device described in conjunction with FIG. 3, the evacuation shortly before use is extremely simple and inexpensive. Evacuation mechanism 19, from the standpoint of cost, basically comprises the vacuum pump, which is relatively inexpensive and simple.

These characteristics of the blood extraction system in accordance with the present invention makes it possible to predesign the sealing, determined by the thickness of membrane 18 as well as the sealing surface and the contact pressure, in such a manner that the sealing need maintain the desired vacuum over only a relatively short period of time, approximately a maximum two or three days. This is advantageous in that the invention eliminates the traditionally used rubber stopper and uses a simple screw closure. The screw closure can be opened without the occurrence of an "aerosol" effect which occurs when a rubber stopper is removed.

Figure 5:
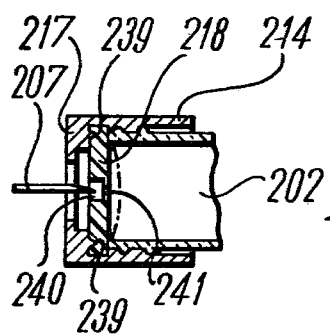
FIG. 5 illustrates another embodiment of the present invention, and particularly illustrates a particular embodiment of a sealing membrane 218.

In the embodiment shown in FIG. 5, edge 217 of cap 214 has a small, circumferencial path 239 with a relatively sharp edge which connects with the surface of membrane 218 and holds it in place. This may be the case when the membrane is so thin that it is drawn into blood sample tube 202, to the position indicated with a dotted line. In the middle, at the point where it is penetrated by needle 207, membrane 218 has a recess 240, so that needle 207 need only penetrate thin portion 241.

Figure 6:
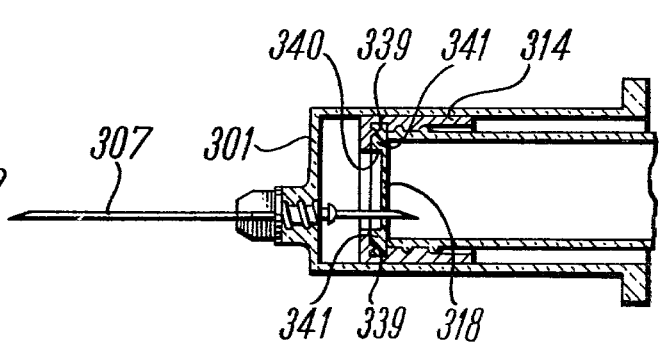
FIG. 6 illustrates another embodiment of the invention, particularly illustrating another form of a sealing membrane.

Referring now to the embodiment shown in FIG. 6, the recess in membrane 318 is much larger than in the embodiment of FIG. 5. One can only see a bead shaped collar at its edge, which connects with path 339 of cap 314. As in FIG. 1a and FIG. 4b, needle 307 is eccentrically placed in receptacle 301. This facilitates insertion into a vein.

Figure 7:
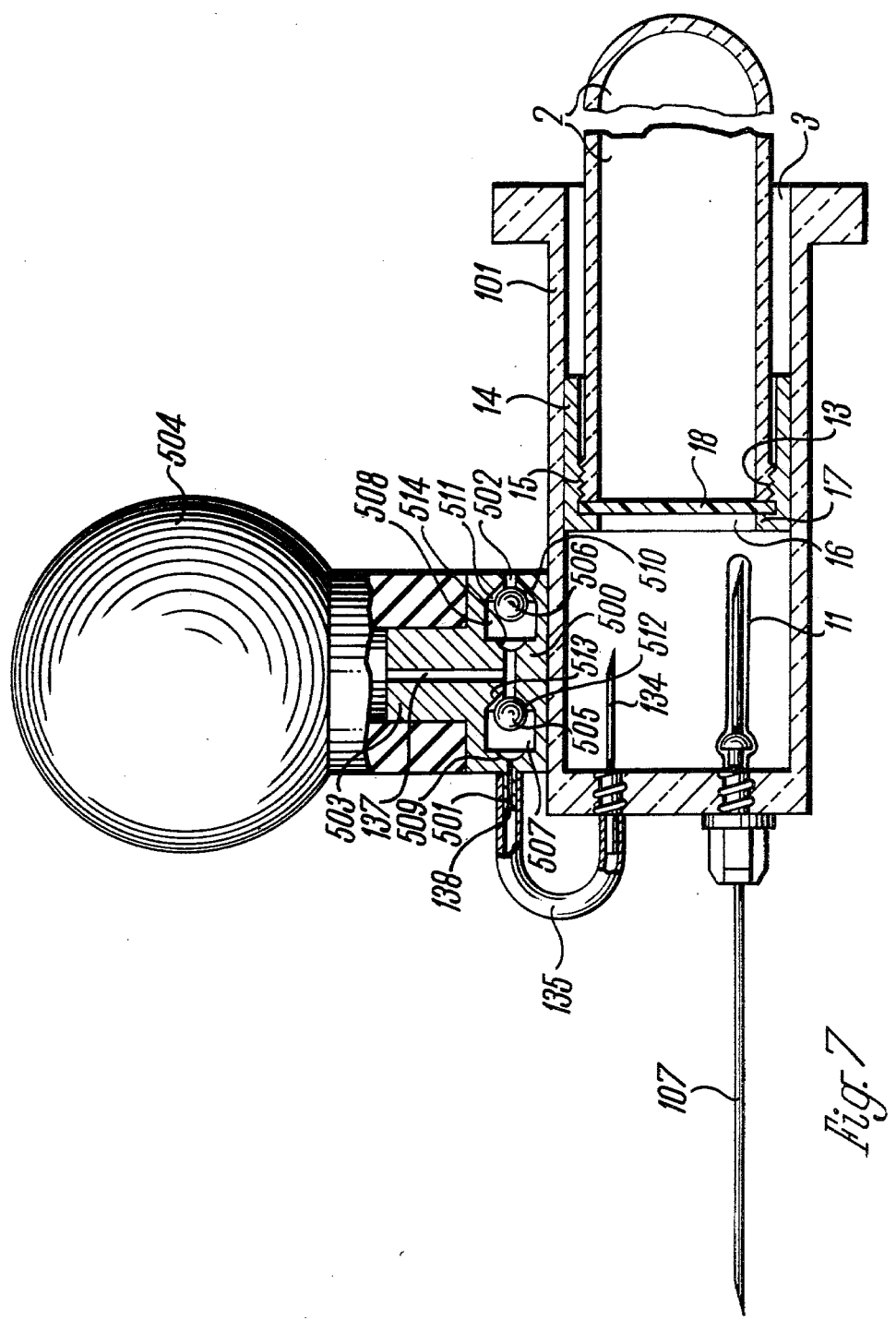
FIG. 7 is an elevation view, partially in cross-section, of another embodiment of the present invention.

The blood extraction system according to FIG. 7 represents a further development of the blood extraction device according to FIGS. 4a—4c. It is constituted by receptacle 101 and blood sample tube 2. Suction line 137 is connected with three-way valve 500 via connecting plug 138. A second opening 501 leads to connection 138. A third opening 502 communicates with the atmosphere. On connector 503, in which suction line 137 is provided, compressible rubber balloon 504 has been applied. After compression, it has the tendency to regain the round shape as illustrated. Thus, a pump effect can be obtained, which can be utilized for so-called aspiration, e.g. blood extraction with simultaneous creation of additional negative pressure in blood sample tube 2.

In the embodiment shown, valve 500 is designed as a double ball valve with two balls, 505 and 506, which are located in valve chambers 507 and 508. If rubber balloon 504 is compressed, an over-pressure occurs in suction line 137. Ball 505 in left-hand chamber 507 is pushed to valve seat 509 and closes it. Thus, no air can exit into line 135 and consequently not into blood sample tube 2. Simultaneously, right-hand ball 506 in chamber 508 is pressed against right-hand valve seat 510. However, valve seat 510 is not solidly formed but is provided with a slit 511 by means of which air can escape and enter the atmosphere via opening 502. When rubber balloon 504 is compressed, opening 501 is closed and thereby also the access to needle 134. The air which is dislocated when balloon 504 is compressed escapes into the atmosphere via opening 502.

If the compressed rubber balloon 504 is released, a negative pressure occurs in suction line 137. The two balls 505 and 506 are drawn inwardly. Ball 505 locates on valve seat 512. However, air from line 501 can travel into suction line 137 via two slits 513. Thus, a negative pressure, and a suction effect, are created in blood sample tube 2. On the other hand, ball 506 closes valve seat 514 so that opening 502 is closed.

In this manner, the negative pressure created in blood sample tube 2 can be controlled by hand-operated release of rubber balloon 504.

It is emphasized that valve 500 as illustrated is merely a preferred embodiment and is not intended to limit the invention. Any suitable valve may be used which guarantees that only a negative pressure is created via hollow line 135 and second needle 134 in blood sample tube 2, and which ensures that no air is pushed into blood sample tube 2 when the rubber balloon is compressed.

As shown in FIG. 8, rubber balloon 504 may also be utilized as a handle for easier operation of the blood extraction device for extracting blood from vein V of arm A.

The embodiment shown in FIG. 9 differs from that shown in FIG. 7 in that rubber balloon 515 is designed as a fish bladder and is adjacent to receptacle 101 in such a manner that it enables handling with only one hand in a particularly simple manner. This is shown in FIG. 10.

In view of the above, the present invention may be embodied in other specific forms without departing from the spirit of essential attributes thereof and, accordingly, reference should be made to the appended claims, rather than to the foregoing specification as indicating the scope of the invention.

I claim:
1. A blood extraction device, comprising:
a hollow, cylindrical receptacle, said receptacle being provided at one end with a double ended hollow needle passing therethrough, one end of said needle extending into the hollow cylindrical space of said receptacle and the other end of said hollow needle being located outside of said receptacle, the opposite end of said hollow, cylindrical receptacle being open;
a blood sample tube being closed at one end with a seal which may be penetrated by a needle, said sealed end of said blood sample tube being slidably inserted into the hollow cylindrical space of said receptacle so that said one end of said needle which extends into the space of said receptacle penetrates said seal to create a connection between the inte- rior of said blood sample tube and the other end of said needle; and said seal of said blood sample tube being comprised of a flat sealing membrane of a material that may be penetrated by one end of said needle when inserted into said cylindrical receptacle, said membrane being retained by a releasably screw attaced cap having threads adapted to mate with threads on said blood sample tube, said cap being provided with an opening therein so that said needle may pass through said membrane, a rim being provided around said opening in said cap, said sealing membrane being retained by said rim to form said seal.

2. A blood extraction device in accordance with claim 1 wherein the thickness of said sealing membrane is in the range of 1.5 to 3 milimeters.

3. A blood extraction device in accordance with claim 1 wherein the thickness of said sealing membrane is approximately 2 milimeters.

4. A blood extraction device in accordance with claim 1 wherein said needle is mounted eccentrically on the closed end of said receptacle.

5. A blood extraction device in accordance with claim 1 wherein said blood sample tube is not evacuated until shortly prior to usage, an evacuation device, said evacuation device being provided with a hollow needle for penetrating said sealing membrane of said blood sample tube, said hollow needle being connected to a source of vacuum.

6. A blood extraction device in accordance with claim 5 wherein said evacuation device is provided with a pressure sensitive switching device which automatically turns off said vacuum source when a pre-determined value of vacuum has been reached.

* * * * *